United States Patent [19]

Chikashige et al.

[11] 4,271,845
[45] Jun. 9, 1981

[54] DEVICE FOR BENDING A MEDICAL INSTRUMENT INSERTED INTO THE BODY CAVITY

[75] Inventors: Kiyoshi Chikashige, Tsurugashima; Nagashige Takahashi, Tokyo, both of Japan

[73] Assignee: Kabushiki Kaisha Medos Kenkyusho, Tokyo, Japan

[21] Appl. No.: 54,115

[22] Filed: Jul. 2, 1979

[30] Foreign Application Priority Data

Jul. 1, 1978 [JP] Japan .................................. 53-80039

[51] Int. Cl.³ .............................................. A61B 10/00
[52] U.S. Cl. ...................................... 128/756; 128/4; 128/328
[58] Field of Search ............................... 128/749–759, 128/772, 656–657, 658, 3, 4, 303 R, 303.15, 321, 328, DIG. 9

[56] References Cited

U.S. PATENT DOCUMENTS

| 3,452,740 | 7/1969 | Muller | 128/772 |
| 3,452,742 | 7/1969 | Muller | 128/2 |
| 3,521,620 | 7/1970 | Cook | 128/772 |
| 3,613,664 | 10/1971 | Willson | 128/756 |
| 3,749,085 | 7/1973 | Willson et al. | 128/757 |
| 3,805,767 | 4/1974 | Erb | 128/1 R |
| 3,964,468 | 6/1976 | Schulz | 128/751 |
| 3,973,556 | 8/1976 | Fleischhacker et al. | 128/772 |
| 4,020,829 | 5/1977 | Willson et al. | 12/772 |
| 4,215,703 | 8/1980 | Willson | 128/772 |

*Primary Examiner*—Robert W. Michell
*Assistant Examiner*—Nancy B. Swisher
*Attorney, Agent, or Firm*—Sughrue, Rothwell, Mion, Zinn and Macpeak

[57] ABSTRACT

A device for bending a medical instrument inserted into the body cavity having a flexible cylindrical coil formed by winding an elastic thin wire. The flexible cylindrical coil has a coarsely wound portion at one end portion thereof, that is designed by changing configuration or material so that one side of the coarsely wound portion is different in cross sectional area from the other side which is diametrically opposite. When a pulling string directly or indirectly fastened to the coarsely wound portion of the flexible cylindrical coil is operated, the turns of said flexible cylindrical coil are brought closer to each other on the side of the coarsely wound portion greater in torsional strength to thereby bend the one end portion of the flexible cylindrical coil towards the side of the coarsely wound portion.

6 Claims, 9 Drawing Figures

DEVICE FOR BENDING A MEDICAL INSTRUMENT INSERTED INTO THE BODY CAVITY

BACKGROUND OF THE INVENTION

This invention relates to a device for bending a bioptic instrument which is used with an endoscope for sampling the cells or tissues of a diseased portion in the body cavity, or a medical instrument such as an insertion tube which is inserted into the body cavity.

A bioptic instrument, such as for instance forceps, of this type which is used with an endoscope is inserted into the flexible pipe of the endoscope. The tissue sampling instrument protrudes from the end of the flexible pipe towards the diseased portion in the body cavity, to thereby bite or excoriate the diseased portion to sample the tissues.

Heretofore, the sampling instrument is directed towards the diseased portion by bending the body of the endoscope. However, it is difficult to sharply bend the body of the endoscope because the flexible pipe of the body of the endoscope includes a light conducting pipe, a gas or water delivering pipe, and a bioptic instrument inserting pipe. Therefore, it is relatively larger in diameter.

In sampling the tissues with forceps, the forceps' cups must correctly confront the diseased portion in the body cavity to be examined. However, it is difficult to sample all of the portions in the body cavity merely by the bending operation of the body of the endoscope.

In order to eliminate this difficulty, a bioptic instrument bending device has been proposed in which the pipe is relatively small in diameter and can be readily bent, so that its end portion can be curved for operation. Such a bioptic instrument has been put in practical use.

In one example of the conventional bioptic instrument bending device, the end portion of the flexible pipe is in the form of a coil obtained by coarsely winding a metal wire. A stay wire is fastened to one side of the coil end, while one end of a pulling string is fastened to the opposite side of the coil end. In another example of the conventional bioptic instrument bending device, one side of such a coarsely wound coil is subjected to electrolytic abrasion to reduce the diameter of the coil forming wire on that side so that the coarsely wound coil can be bent towards the side where the diameter of the coil forming wire is reduced.

In the former example of the conventional bending device, one end of the stay wire is brazed to a part of the coil, and therefore the bending characteristic of the coil is lowered by the brazed part. Therefore, for instance, in the case where the bioptic instrument is inserted into the endoscope which has been bent in the body cavity for observing the portion to be examined, it is difficult to insert it thereto, and sometimes the inside of the endoscope may be damaged. Furthermore, when in the bending device using the stay wire of this type, the coil is bent by operating the pulling string, the pulling force is the sum of the coil bending force and the stay wire folding force. Hence, the force exerted on the pulling string is increased as much, thereby decreasing the durability of the pulling string. In order to increase the durability, it is necessary to increase the strength of the pulling string by increasing its diameter. However, this is not preferable, because the coil becomes necessarily bulky.

In the latter example of the conventional bending device, one side of the coil is subjected to electrolytic abrasion. Therefore, both the inner and outer surfaces of the coil subjected to electrolytic abration are eroded to be rough. The portion of the coil thus eroded may be weakened in mechanical strength and may be further eroded by acidic liquid. Thus, its durability is quite low. In addition, it is difficult to obtain a coil uniform in quality for the bending device.

SUMMARY OF THE INVENTION

Accordingly, an object of the invention is to eliminate all of the above-described drawbacks accompanying a conventional bending device.

More specifically, an object of the invention is to provide a bending device based on a novel dynamic consideration as a coarsely wound coil, in which the flexible end portion of a medical insertion instrument which is inserted into the body cavity can be sufficiently bent by applying a relatively small force to its pulling string at the manual operation section of an endoscope.

These and other objects of this invention are accomplished in a device for bending a medical instrument inserted into the body cavity having a flexible cylindrical coil formed by winding an elastic thin wire. The flexible cylindrical coil has a coarsely wound portion at one end portion thereof that is designed by changing configuration or material so that one side of the coarsely wound portion is different in cross sectional area from the other side which is diametrally opposite. When a pulling string directly or indirectly fastened to the coarsely wound portion of the flexible cylindrical coil is operated, the turns of said flexible cylindrical coil are brought closer to each other on the side of the coarsely wound portion greater in torsional strength to thereby to bend the one end portion of the flexible cylindrical coil towards the side of the coarsely wound portion.

This invention will now be described with reference to its preferred embodiments and the drawings.

DESCRIPTION OF THE PREFERRED EMBODIMENTS

Figure 1:
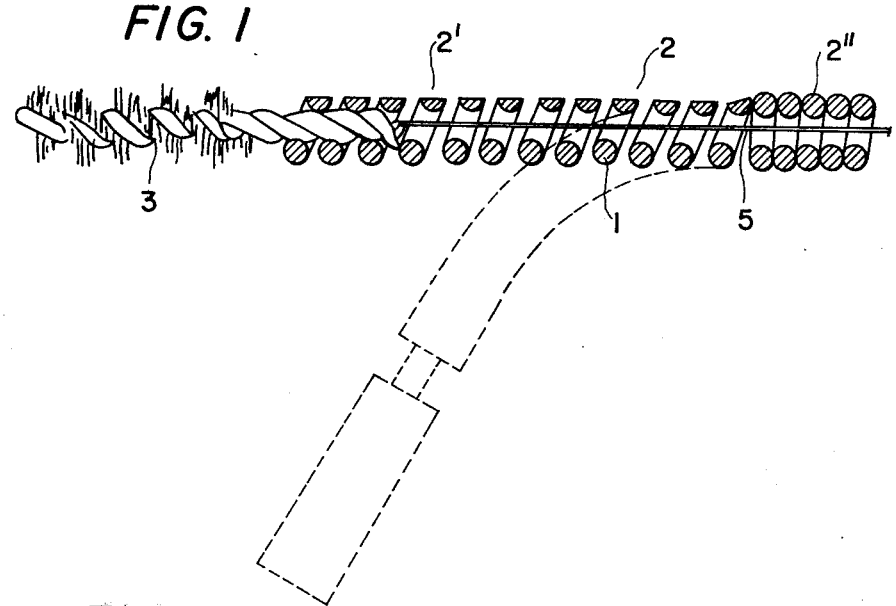
FIG. 1 is a longitudinal sectional view of one example of a device for bending a medical instrument to be inserted into the body cavity, according to the invention.
Figure 2:
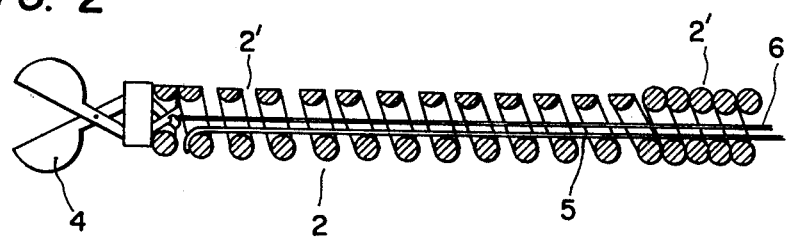
FIG. 2 is also a longitudinal sectional view of a second example of the device according to the invention.

FIG. 1 is a longitudinal sectional view of one example of a device for bending a medical instrument to be inserted into the body cavity, according to the invention. FIG. 2 is also a longitudinal sectional view showing a different mounting state of the device according to the invention. A cylindrical coil 2 is formed by winding an elastic thin wire 1 of metal or hard plastic. More specifically, one end portion 2' of the coil 2 is obtained by coarsely winding the wire (hereinafter referred to as "a coarsely wound portion 2'" when applicable), while the remaining longer portion 2" is obtained by finely winding the wire (hereinafter referred to as "a finely wound portion 2''" when applicable). Hence, a pipe is formed which is flexible over its length. An excoriating brush 3 or a forceps 4 is secured to one end of the flexible pipe thus formed.

In the example shown in FIG. 1, the excoriating brush 3 is secured to the end of the flexible pipe, and one end of a pulling string 5 adapted to bend the flexible pipe is fixedly secured to the mounting end of the brush by brazing or the like. In the example shown in FIG. 2, the forceps 4 is secured thereto, and a pulling string 5 is secured to one side of the end of the cylindrical coil 2. In the case of FIG. 2, in addition to the pulling string 5, a second pulling string 6 is arranged in the cylindrical coil 2.

In the device according to the invention, one side of the coarsely wound portion 2' of the cylindrical coil 2 is cut so that the section of the thin wire 1 forming that portion 2' is substantially semi-circular.

Figure 3:
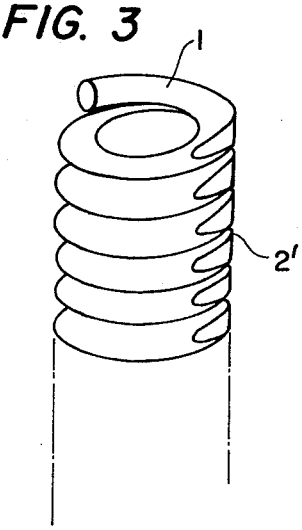
FIG. 3 is an enlarged perspective view showing a coarsely wound portion of the device according to the invention.

FIG. 3 is an enlarged view of the coarsely wound portion 2'. One side of the coarsely wound portion 2' of the cylindrical coil 2' is ground flat as shown.

Figure 4:
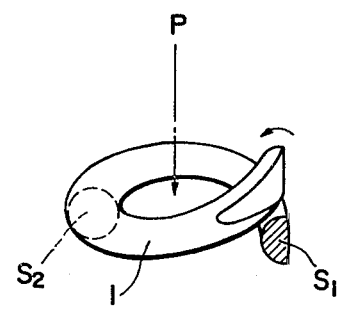
FIG. 4 and FIG. 5 are perspective views showing a part of the coarsely wound portion of the device according to the invention.
Figure 5:
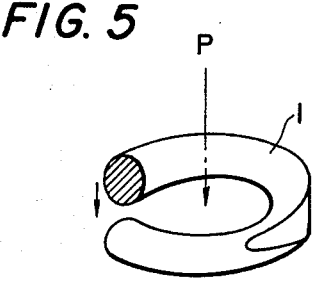
Figure 9:
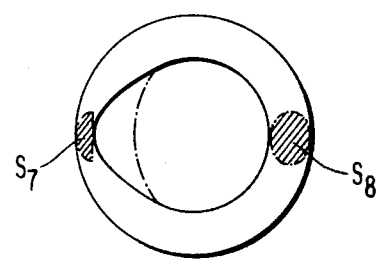

FIGS. 4 and 5 are perspective views showing one turn of the coarsely wound portion 2 cut as described above. These figures are intended to show that the sectional area $S_1$ of a portion of the thin wire 1, whose outer side has been cut, is smaller than the sectional area $S_2$ of a portion of the thin wire 1, which is diametrally opposite to the firstly-mentioned portion. As an alternative, FIG. 9 illustrates the coarsely wound portion having a portion cut-out of the inside of the winding to produce the cross-sectional areas $S_7$ and $S_8$.

Figure 6:
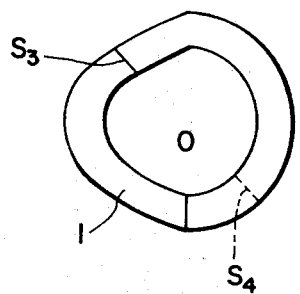
FIG. 6, FIG. 7 and FIG. 9 are plan views showing two other examples of the device according to the invention.

FIG. 6 is a plan view showing another example of the coarsely wound portion 2' in the device according to the invention. One side of the coarsely wound portion 2' is deformed so that the sectional area $S_3$, taken along the line passing through the center of the winding center 0, of the deformed portion of the coarsely wound portion 2' is larger than the sectional area $S_4$ of a portion of the coarsely wound portion 2', which is not deformed and is diametrally opposite to the deformed portion.

Figure 7:
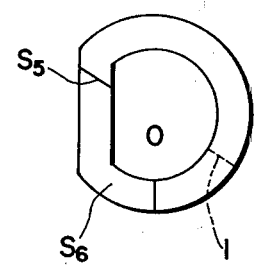

FIG. 7 shows another example of the coarsely wound portion 2' in the device according to the invention. In this case the coarsely wound portion 2' is deformed so that the sectional area $S_5$ of the deformed portion is larger than that $S_6$ of the portion which is not deformed. The coarsely wound portion 2' may be deformed so that it has a wavy portion or the thin wire 1 is variable in section.

Figure 8:
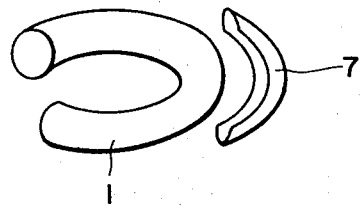
FIG. 8 is a perspective view showing a further example of the device according to the invention.

FIG. 8 shows another example of the coarsely wound portion 2 in the device according to the invention. Reinforcing pieces 7 are fixedly secured to one side of the coarsely wound portion in such a manner that each reinforcing piece 7 covers substantially one half circumference of each turn of the coil. In the case where the thin wire 1 is a metal wire, the reinforcing pieces 7 may be formed by brazing or plating. In the case where the thin wire 1 is a plastic wire, the reinforcing pieces 7 may be bonded to the respective portions of the coil, or may be imbedded in the thin wire 1 by molding or the like.

In general, in the flexible cylindrical coil obtained merely by coarsely winding a metal thin wire or the like, when a compression force is applied longitudinally of the coil and towards the center thereof, it is uniformly exerted on all of the turns of the coil. As a result, the turns of the coil are uniformly brought closer to one another. That is, the length of the coil is reduced, but the coil is not bent. However, in the case where one end of a pulling string inserted into the coil is fastened to one side of the coil end, which is spaced from the winding center, and a compression force is applied to the coil by pulling the string, then the coil is bent towards the side of the coil where the pulling string has been fastened. This bending force is increased as the point where the pulling string is fastened is moved further away from the winding center.

However, since the cylindrical coil used for the above-described medical operation is small in diameter, it is impossible to set the pulling string fastening point significantly apart from the winding center of the coil. Therefore, with such a bending technique, the bending operation is carried out while contracting the coil itself. Therefore, the angle length (the length of the bend portion) is short. Therefore, it is impossible to sharply bend the coil.

On the other hand, in the device according to the invention described above, as shown in FIGS. 1 through 5, one side of the cylindrical coil 2 is cut so that the sectional area $S_1$ of the portion thus cut is smaller than the sectional area $S_2$ of the portion which has not been cut.

When a compression force P is exerted on the center of the cylindrical coil 2 is in the longitudinal direction thereof, then a torsional action occurs with the wound thin wire 1 moving in the direction of contraction of the cylindrical coil. The stress of the thin wire 1 corresponding to the torsional action is proportional to the square of the sectional area $S_1$ and $S_2$. The thin wire is readily twisted owing to the difference between the sectional areas $S_1$ and $S_2$. That is, the thin wire can be readily twisted because the torsional stress for the sectional area $S_1$, of the portion which is cut, is smaller than that for the sectional area $S_2$, of the portion which is not cut.

Thus, the cut portion of the cylindrical coil 2 is twisted in the direction of the small arrow in FIG. 4 by the compression force uniformly applied to the entire thin wire 1 which is wound in the form of a coil. As a result, the opposite side is moved in the direction of the small arrow as shown in FIG. 5. As a result of this motion, the portions having the larger sectional area $S_2$ of the cylindrical coil 2 are brought closer to one another, and therefore the cylindrical coil 2 is bent in that direction. Since the bending operation in this case is based on the local difference in torsional stress between the portions of the coiled thin wire, the bending operation is effectuated as soon as the compression force is applied to the cylindrical coil. Furthermore, the length of the cylindrical coil 2 is not significantly reduced. Accordingly in this case, it is unnecessary to increase the angle length to shaply bend the cylindrical coil 2.

In the device according to the invention, the bending operation can be effectively carried out even for the cylindrical coil 2 in which the compression force is applied to the center of the cylindrical coil (FIG. 1). However, the bending operation is more effectively carried out for the cylindrical coil where the compression force is applied to the side of the coil end, which is opposite to the cut side of the coil end (FIG. 2).

In the example shown in FIG. 6 or 7, the torsional stress of the portion having the sectional areas $S_3$ or $S_5$ of the thin wire 1 is greater than that of the other portion, and the former portion is hardened by the deformation. Therefore, the former portion is relatively untwistable. However, since the other portion is relatively twistable, the turns of that portion are brought closer to one another, and the cylindrical coil 2 is bent towards that portion.

In the example shown in FIG. 8, the torsional stress of the side of the cylindrical coil, which has the reinforcing pieces 7, is greater than that of the other side. Accordingly, the coil turns on the former side are brought closer to one another, and the cylindrical coil 2 is bent towards this side.

If the device according to this invention is applied to a conventional single or plural articulation type culet device, then the bending operation of this invention is added to the inherent articulating operation of the end culet section thereof. As a result, more intricate articulating operations are available. Accordingly, tissues can be more effectively sampled, and the insertion instrument can be more suitably introduced into branch pipe 5 of the body cavity to be examined. (i.e. portions of lung tissue, etc.)

As is apparent from the above description, in the device according to the invention, one side of the flexible cylindrical coil obtained by coarsely winding the thin wire is different in torsional stress from the opposite side thereof. Therefore, when a compression force is applied to the flexible cylindrical coil, the portion smaller in torsional stress thereof is readily twisted, while the coil turns of the other portion are brought closer to one another. As a result, the cylindrical coil is positively bent towards the side where the torsional stress is greater. In this case, the cylindrical coil is not reduced in length. Therefore, the cylindrical coil can be sharply bent with the necessary angle length.

In the conventional device using the stay wire, as the length of the stay wire is reduced, the bending burden per unitary wire length is increased. Therefore, when the bending operation is released, the wire is liable to be still maintained in a bent condition. Accordingly, it is necessary to increase the length of the stay wire.

On the other hand, in the device according to the invention, the bending action is effected by the torsional moment of the wound thin wire itself, and the wound thin wire is sufficiently long for the short cylindrical coil. Therefore the bending moment applied to the unitary length of the thin wire during the bending operation, is small. Accordingly, the thin wire is not deteriorated even if it is used for a long period of time. Furthermore, the angle length can be reduced in the case where it is required to obtain a bending angle similar to that in the conventional device. Thus, the durability of the device can be increased, and the smooth bending operation and the sharp angle bending control can be obtained.

If the device according to the invention is connected to forceps, for the examination of the branched bronchus, it is possible to bend the endoscope to insert it thereinto, and to permit the forceps to enter a branched path which is extended in a direction opposite to the direction in which the endoscope can be bent. Accordingly, the forceps can be introduced into a thin, branched path which the conventional endoscope cannot enter. Thus, with the device according to the invention, the medical insertion instrument can be selectively inserted into portions of the body into which it could not previously be inserted with a conventional device. The device according to the invention can be effectively used for the bioptic instruments, that is instruments to be inserted into the body cavity, and endoscopes.

It is apparent that modifications of the invention can be made without departing from the scope of the invention. For example, the coarsely wound portion may be softened by annealing or a portion hardened by quenching to provide for a difference in torsional strength.

What is claimed is:

1. A device for bending a medical instrument inserted into the body cavity, comprising: a flexible cylindrical coil formed by winding an elastic thin wire and having a longitudinal axis, said flexible cylindrical coil having a coarsely wound portion at one end portion thereof, said coarsely wound portion having a first side and a second side which is diametrically opposite to said first side, said second side having a cut-out portion having a substantially flat profile substantially parallel to said longitudinal axis to thereby provide said first side with a greater torsional strength than said second side; and a pulling string fastened to said coarsely wound portion of said flexible cylindrical coil, whereby when said pulling string is operated, the turns of said flexible cylindrical coil are brought closer to each other on said first side of said coarsely wound portion greater in torsional strength than said second side to thereby bend said one end portion of said flexible cylindrical coil towards said first side of said coarsely wound portion.

2. A device as claimed in claim 1 wherein said first side has a different cross sectional area than said second side.

3. A device as claimed in claims 1 or 2, wherein said second side has said cut-out portion at the outer side thereof.

4. A device as claimed in claims 1 or 2 further comprising a finely wound portion of said flexible cylindrical coil formed as a continuation of one end of said coarsely wound portion.

5. A device as claimed in claim 4 further comprising a forceps attached to the other end of said coarsely wound portion.

6. A device as claimed in claim 4 further comprising an excoriating brush attached to the other end of said coarsely wound portion.

* * * * *